US009119556B2

(12) United States Patent
Nakata et al.

(10) Patent No.: US 9,119,556 B2
(45) Date of Patent: Sep. 1, 2015

(54) ULTRASONIC DIAGNOSTIC APPARATUS (75) Inventors: Masahiko Nakata, Ube (JP); Eiji Kasahara, Mitaka (JP); Masaru Murashita, Mitaka (JP); Yasuhiro Ito, Mitaka (JP)

(73) Assignee: HITACHI ALOKA MEDICAL, LTD., Tokyo (JP)

( * ) Notice: Subject to any disclaimer, the term of this patent is extended or adjusted under 35 U.S.C. 154(b) by 0 days.

(21) Appl. No.: 13/037,538

(22) Filed: Mar. 1, 2011

(65) Prior Publication Data

US 2011/0213249 A1     Sep. 1, 2011

(30) Foreign Application Priority Data

Mar. 1, 2010   (JP) ................... 2010-044012

(51) Int. Cl.
*A61B 8/00*     (2006.01)
*A61B 8/08*     (2006.01)
*G01S 7/52*     (2006.01)

(52) U.S. Cl.
CPC ............... *A61B 8/08* (2013.01); *A61B 8/0883* (2013.01); *A61B 8/0866* (2013.01); *G01S 7/52074* (2013.01)

(58) Field of Classification Search
CPC ...... A61B 8/08; A61B 8/0883; A61B 8/0866; G01S 7/52074
USPC ................................. 600/437–472
See application file for complete search history.

(56) References Cited

U.S. PATENT DOCUMENTS

| | | | | |
|---|---|---|---|---|
| 5,088,498 A | * | 2/1992 | Beach et al. | 600/453 |
| 5,785,654 A | * | 7/1998 | Iinuma et al. | 600/441 |
| 5,797,844 A | * | 8/1998 | Yoshioka et al. | 600/442 |
| 6,673,020 B2 | * | 1/2004 | Okada et al. | 600/454 |
| 7,374,538 B2 | * | 5/2008 | Nightingale et al. | 600/443 |
| 7,422,561 B2 | * | 9/2008 | Kanai et al. | 600/437 |
| 7,766,836 B2 | * | 8/2010 | Waki | 600/443 |

(Continued)

FOREIGN PATENT DOCUMENTS

| | | |
|---|---|---|
| JP | 2003-250804 A | 9/2003 |
| JP | 2005-152192 A | 6/2005 |

(Continued)

OTHER PUBLICATIONS

Definition citation from Mondofacto online medical dictionary.*

(Continued)

*Primary Examiner* — Jonathan Cwern
*Assistant Examiner* — Amelie R Gillman
(74) *Attorney, Agent, or Firm* — Westerman, Hattori, Daniels & Adrian, LLP (57) ABSTRACT An ultrasonic diagnostic apparatus which can measure a time difference of motion between a plurality of sites of a cardiac muscle for the heart of a fetus is provided. On a tomographic image of the heart, a user sets a plurality of observation points. Each observation point is tracked, and a plurality of displacement waveforms representing a temporal displacement of the plurality of observation points are generated. A time difference between a plurality of representative points is calculated between the plurality of displacement waveforms. Such a time difference is displayed as a numerical value or as a graph. The representative point is a peak point, a zero-cross point, an inflection point, or the like. The plurality of observation points are set along conduction pathways in the heart for the electric signal.

4 Claims, 5 Drawing Sheets

(56) References Cited

U.S. PATENT DOCUMENTS

| | | | |
|---|---|---|---|
| 7,775,978 B2* | 8/2010 | Nadadur et al. | 600/437 |
| 8,052,602 B2* | 11/2011 | Sunagawa et al. | 600/437 |
| 8,077,944 B2* | 12/2011 | Schummers | 382/128 |
| 8,118,744 B2* | 2/2012 | Palmeri et al. | |
| 2003/0171668 A1* | 9/2003 | Tsujino et al. | 600/407 |
| 2004/0015081 A1 | 1/2004 | Kramer et al. | |
| 2005/0203395 A1 | 9/2005 | Sui et al. | |
| 2005/0228276 A1* | 10/2005 | He et al. | 600/437 |
| 2006/0074315 A1 | 4/2006 | Liang et al. | |
| 2006/0116576 A1* | 6/2006 | McGee et al. | 600/434 |
| 2007/0004982 A1* | 1/2007 | Marwick et al. | 600/437 |
| 2008/0009735 A1 | 1/2008 | Murashita | |
| 2008/0125652 A1* | 5/2008 | Clark | 600/437 |
| 2009/0018444 A1* | 1/2009 | Osaka et al. | 600/437 |
| 2009/0177101 A1* | 7/2009 | Hersh et al. | 600/511 |
| 2010/0069751 A1* | 3/2010 | Hazard et al. | 600/438 |
| 2011/0144495 A1* | 6/2011 | Wilkening et al. | 600/443 |

FOREIGN PATENT DOCUMENTS

| | | |
|---|---|---|
| JP | 2006-026079 A | 2/2006 |
| JP | 2006-075590 A | 3/2006 |
| JP | 2007-075333 A | 3/2007 |
| JP | 2007-117252 A | 5/2007 |
| JP | 2007-236606 A | 9/2007 |
| JP | 2008-012047 A | 1/2008 |
| WO | 2007/107926 A1 | 9/2007 |

OTHER PUBLICATIONS

Ito, english translation of JP2006026079, cited in IDS dated Dec. 20, 2013.*

European Search Report dated Jun. 24, 2011, issued in corresponding European patent Application No. 11001467.7.

Japanese Office Action dated Oct. 1, 2013, issued in Japanese Patent Application No. 2010-044012, w/English translation.

* cited by examiner

ULTRASONIC DIAGNOSTIC APPARATUS

BACKGROUND

1. Technical Field

The present invention relates to an ultrasonic diagnostic apparatus, and in particular, to a technique for evaluating or measuring conduction of an electric signal in the heart.

2. Background Art

An ultrasonic diagnostic apparatus is an apparatus which forms an ultrasonic image based on a reception signal obtained by transmitting and receiving ultrasound to and from a living body. The ultrasonic diagnostic apparatus generally comprises a probe, a transmitting unit, a receiving unit, an image forming unit, a measuring unit, etc. The concept of the ultrasonic diagnostic apparatus in the present application also includes a computer having an ultrasonic image processing function.

In the human heart, contraction of a cardiac muscle is caused by an electric signal generated in the living body stimulating the cardiac muscle. The electric signal is transmitted in the heart from a sinus node via a plurality of routes to the entirety of the heart. The contraction timings of the right atrium, the left atrium, the right ventricle, and the left ventricle do not match each other. That is, there is a time difference in the motions of the individual cardiac muscle sites in the heart. It can be deduced that, by evaluating such a time difference, it is possible to identify abnormality of the motion of the cardiac muscle or cardiac disease. However, the ultrasonic diagnostic apparatuses of the related art are not equipped with a function to measure such a conduction time difference or a contraction time difference. For the heart of a fetus in the mother's womb, direct measurement of the electrocardiographic signal is difficult. There is desire for a method in which the conduction of the electric signal can be measured for the heart of a fetus.

JP 2007-75333 A discloses an ultrasonic diagnostic apparatus having a function to track an observation point designated by a user by applying a pattern matching (image matching) technique between adjacent frames. The tracking is two-dimensional tracking.

As described, there is desire to measure conduction of the electric signal in a heart (in particular, the heart of a fetus). This is because a cardiac muscle motion is primarily observed with the eyes on a two-dimensional tomographic image (video image) of the heart and it is difficult to identify abnormality of an electric signal conducting system or abnormality of the cardiac muscle motion. In order to diagnose a disease of the heart, it is desired to objectively or quantitatively evaluate such abnormality.

SUMMARY

An advantage of the present invention is provision of an ultrasonic diagnostic apparatus which can quantitatively evaluate the conduction of the electric signal in the heart.

According to one aspect of the present invention, there is provided an ultrasonic diagnostic apparatus comprising a setting unit which sets, on an ultrasonic image of a heart, a plurality of observation points on conduction pathways of the heart for an electric signal which causes contraction of a cardiac muscle; a tracking unit which tracks each of the observation points to determine a temporal displacement of each of the observation points; a waveform generating unit which generates a plurality of displacement waveforms representing the temporal displacements for the plurality of observation points; and an analyzing unit which analyzes the plurality of displacement waveforms on a common time axis to calculate a time difference of motion for the plurality of observation points.

According to the above-described configuration of the present invention, on an ultrasonic image of the heart, a plurality of observation points are set on the conduction pathways of the heart, and each observation point is tracked to determine the temporal displacement of each observation point. For each observation point, a displacement waveform (that is, a displacement data array) is generated based on the temporal displacement each time. The plurality of displacement waveforms are analyzed on a common time axis, to calculate a time difference of motion caused among the plurality of observation points. The time difference of motion is provided to the user in a form of a numerical value, a graph, or the like. Based on such a time difference of motion, it becomes possible to objectively or quantitatively diagnose the conduction of the electric signal and the characteristic of cardiac muscle. This method is particularly desirably applied to the heart of a fetus for which the electrocardiographic signal cannot be directly measured. If the heart function measurement can be realized as a diagnosis of a fetus before birth, it becomes possible to quickly and accurately prepare for the disease of the heart of the fetus after birth, based on the measurement result. Therefore, the present invention provides a significant advantage in the medical field.

The displacement measured as the result of the tracking may be a one-dimensional displacement, a two-dimensional displacement (two-dimensional displacement vector), or an absolute value of the two-dimensional displacement. Alternatively, the displacement may be a three-dimensional displacement. Alternatively, the displacement measuring direction may be individually determined for each observation point. Alternatively, the displacement measuring direction may be determined as a direction where each observation point is present, as viewed from a common reference point (for example, the center of gravity of the heart). In the measurement of the displacement, the displacement measuring direction is desirably determined such that a translational motion component of the heart is cancelled or compensated for. For the tracking or displacement calculation of the observation point, there may be employed various known methods such as an inter-frame matching, an ultrasonic Doppler method, and an echo tracking method which measures a phase change. Desirably, the inter-frame matching is applied and a two-dimensional motion vector between frames is calculated. The matching calculation may be executed between adjacent frames, or the matching calculation may be applied between a reference frame and each subsequent frame. In either case, the motion of the observation point is successively observed. The plurality of observation points can be arbitrarily determined, but are desirably determined as points that are significant in the disease diagnosis. The observation points may include points indicating sinus nodes corresponding to a source of the electric signal, or points near the sinus node. In either case, the time difference of motion is evaluated between a plurality of observation points. In this case, for example, the difference in timing of start of contraction is calculated. In general, it is desirable to determine an observation point proximal to the sinus node and an observation point distal from the sinus node.

According to another aspect of the present invention, it is desirable that, in the ultrasonic diagnostic apparatus, the plurality of observation points include a proximal observation point and a distal observation point, the plurality of displacement waveforms include a proximal displacement waveform corresponding to the proximal observation point and a distal displacement waveform corresponding to the distal observation point, and the analyzing unit calculates, as the time difference of motion, a relative delay of the distal displacement waveform with respect to the proximal displacement waveform. The proximal observation point is a first observation point and the distal observation point is a second observation point. Alternatively, other observation points may be determined. A plurality of observation points in which the contraction motion is caused at the same temporal timing may be set, but desirably, two points including an upstream side site and a downstream side site in the electric signal conduction system are determined as the observation points. Such two points are the proximal observation point and the distal observation point. "Proximal" and "distal" with regard to the two observation points refer to the temporal proximity, and do not necessarily correspond to proximity in the distance. It is expected that with the accumulation of future clinical research using the present invention, more accurate observation points will be found.

According to another aspect of the present invention, it is preferable that, in the ultrasonic diagnostic apparatus, the analyzing unit comprises a first waveform analyzing unit which analyzes the proximal displacement waveform to identify a generation timing of local contraction caused by arrival of the electric signal as a proximal contraction timing, a second waveform analyzing unit which analyzes the distal displacement waveform to identify a generation timing of local contraction caused by arrival of the electric signal as a distal contraction timing, and a time analyzing unit which measures a time difference between the proximal contraction timing and the distal contraction timing to calculate the time difference of motion. In the analysis of each displacement waveform, a representative point is identified for each heartbeat. The representative point is determined, for example, as a peak point, an inflection point, a zero-cross point, etc., from the viewpoint of the waveform analysis, and, desirably, a point representing the muscle contraction start timing due to arrival of the electric signal or a timing corresponding to such a start timing is identified as the representative point.

According to another aspect of the present invention, it is preferable that, in the ultrasonic diagnostic apparatus, the analyzing unit comprises a sorting processor which executes a sorting process to sort the waveforms for each heartbeat during the analysis of the proximal displacement waveform and the distal displacement waveform, and the time difference of motion is calculated for each heartbeat after the sorting process is executed. With this configuration, because the sorting process or dividing process is applied in advance, a time difference between a plurality of representative points at the same heartbeat can be determined without an error.

According to another aspect of the present invention, it is preferable that the ultrasonic diagnostic apparatus further comprises a unit which determines a displacement measuring direction for each of the observation points. With this configuration, the displacement component at the set displacement measuring direction is measured. The displacement measuring direction is determined, for example, as a direction connecting the center-of-gravity point of the heart and the observation point or a direction connecting a fixedly determined point and the observation point. A direction setting condition is desirably determined such that the direction is not affected by the translational motion of the heart, or the translational motion of the heart is cancelled.

According to another aspect of the present invention, it is preferable that the ultrasonic diagnostic apparatus further comprises a display which displays a displacement waveform image having the plurality of the displacement waveforms arranged in a predetermined order in parallel to the common time. The plurality of displacement waveforms may be displayed in an overlapping manner while a completely common axis is employed for the vertical axis, but, in order to visually easily recognize the time difference, it is desirable to arrange the displacement waveforms by shifting the vertical axis (that is, the axis indicating the amount of displacement or degree of displacement) in the vertical direction while employing a common horizontal axis (time axis) for the plurality of displacement waveforms. In other words, it is desirable to display the plurality of displacement waveforms arranged in the vertical direction. In this case, the plurality of displacement waveforms may be arranged in an order such as the order of magnitude of the arrival time of the electric signal so that the time difference of motion of each site can be easily recognized.

According to another aspect of the present invention, it is preferable that the ultrasonic diagnostic apparatus further comprises a unit which displays, in a combined manner on the displacement waveform image, a plurality of connecting curves across the plurality of displacement waveforms, wherein each of the connecting curves is a curve connecting a plurality of representative points for each heartbeat of the plurality of displacement waveforms. With this configuration, the time difference of motion can be spatially understood. In addition, in a case where the time difference of motion differs for each heartbeat, the difference can be easily recognized as a difference in a shape or a slope of the connecting curve.

DESCRIPTION OF EMBODIMENT

A preferred embodiment of the present invention will now be described with reference to the drawings.

Figure 1:
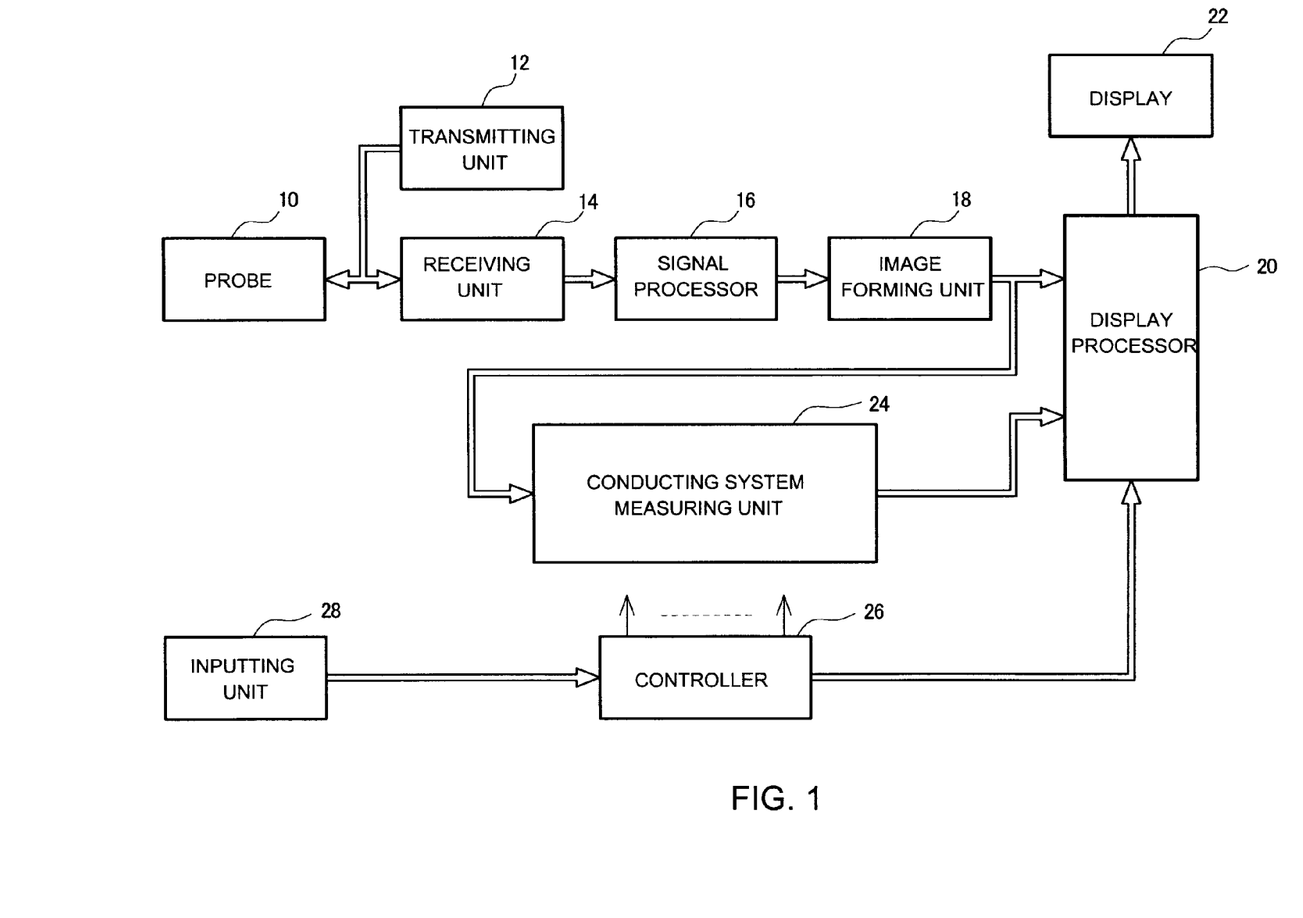
FIG. 1 is a block diagram showing an ultrasonic diagnostic apparatus according to a preferred embodiment of the present invention.

FIG. 1 shows an ultrasonic diagnostic apparatus according to a preferred embodiment of the present invention, and is a block diagram showing an overall structure of the ultrasonic diagnostic apparatus. The ultrasonic diagnostic apparatus is used in the medical field, and executes an ultrasonic diagnosis with respect to the heart or the like. In the present embodiment, the heart for which the ultrasonic diagnosis is applied is the heart of a fetus in a mother's womb. Alternatively, the present invention can be applied to general hearts other than the heart of a fetus. The measurement and image processes of the present invention may be executed on a computer. In such a case, the computer is understood to be the ultrasonic diagnostic apparatus.

In FIG. 1, a probe 10 is an ultrasonic probe which transmits and receives the ultrasound. In the present embodiment, the probe 10 comprises a 1-D array transducer. An ultrasonic beam is formed by the array transducer, and a scan plane which is a two-dimensional echo data capturing space is formed by an electric scanning of the ultrasonic beam. The electronic scanning methods such as electric linear scanning, electronic sector scanning, etc. are known. Alternatively, the probe 10 may be a 3-D probe. Such a 3-D probe comprises a 2-D array transducer; that is, a plurality of transducer elements arranged in a two-dimensional array. The ultrasonic beam is formed by the 2-D array transducer, and is electrically scanned in a first direction and a second direction. With this process, a three-dimensional echo data capturing space is formed, and volume data which is a collection of echo data is obtained from such a three-dimensional space. Alternatively, in place of the 2-D array transducer, a 1-D array transducer and a mechanism which mechanically scans the 1-D array transducer may be provided.

In the present embodiment, the probe 10 is brought into contact with a surface of the abdominal region of a pregnant woman, and transmission and reception of the ultrasound are executed by the probe 10 contacted in this manner. The contact position and contact orientation of the probe 10 are adjusted such that the scan plane is positioned on a desired cross section in the heart of the fetus. Alternatively, there may be used a probe which is inserted into a body cavity.

A transmitting unit 12 functions as a transmission beam former, and supplies, in parallel, a plurality of transmission signals to the array transducer. With this configuration, a transmission beam is formed by the array transducer. A reflected wave from the living body is received by the array transducer, and a plurality of reception signals are output from the array transducer to a receiving unit 14. The receiving unit 14 functions as a reception beam former, and, with a phase-alignment and summing process performed on the plurality of reception signals in the receiving unit 14, beam data (received signal after the phase alignment and summing) are generated. With this process, a reception beam is electrically formed.

A signal processor 16 applies various signal processes such as logarithmic compression and filtering on the beam data, and the beam data after the signal processes are output to an image forming unit 18. The image forming unit comprises a digital scan converter (DSC) having functions for a coordinate conversion process and an interpolation process. The image forming unit 18 forms a two-dimensional tomographic image (B-mode tomographic image) representing a predetermined cross section of the heart based on a plurality of beam data forming one frame. The image data which are output from the image forming unit 18 are output to a display processor 20. In addition, the image data which are output from the image forming unit 18 are also output to a conducting system measuring unit 24 to be described later.

When the echo data obtained from the three-dimensional space are processed, as the image forming unit 18, a 3-D memory, a coordinate conversion unit, a three-dimensional image forming unit, a tomographic image forming unit, etc. are provided. In other words, volume data are formed by mapping the beam data into the three-dimensional space. Based on the volume data, a three-dimensional image and a two-dimensional tomographic image are formed. The latter image is formed using data corresponding to an arbitrary cut plane which is set for the three-dimensional space. The measurement to be described below may be executed based on an image which is formed in real time, or, alternatively, the measurement to be described below may be executed based on data which are read from a cine-memory or the like, or a reproduced image based on such data.

The display processor 20 has an image combining function or the like, and outputs image data to a display 22. The display 22 displays the tomographic image or the like. In addition, an image including the plurality of displacement waveforms or the like to be described below is displayed as necessary.

The conducting system measuring unit 24 is a module which measures the time difference of motion between a plurality of observation points determined on the conductive pathways of the heart for the electric signal. In the present embodiment, a frame array or a frame line which is output from the image forming unit 18 is input to the conducting system measuring unit 24. The frame array comprises a plurality of frames arranged on the time axis, and each frame corresponds to one tomographic image. Alternatively, a frame array before coordinate conversion which is input to the image forming unit 18 may be input to the conducting system measuring unit 24. In this case, each frame comprises a plurality of sets of beam data. The conducting system measuring unit 24 may be realized as a function of software, or may be realized by hardware. Specific processes of the conducting system measuring unit 24 will be described later in detail with reference to FIG. 3. Image data or numerical data obtained as a result of the process are sent through the display processor 20 to the display 22.

A controller 26 comprises a CPU and an operation program or the like, and controls the operations of the elements shown in FIG. 1. In addition, the controller 26 also has a function of generating a graphic image, and the image data are sent to the display processor 20. An inputting unit 28, i.e., a setting unit, which is connected to the controller 26 comprises an operation panel, and the operation panel comprises a keyboard, a track ball, etc. A user can set the plurality of observation points using the inputting unit 28. Alternatively, the setting of the observation points may be automated by image analysis.

Figure 2:
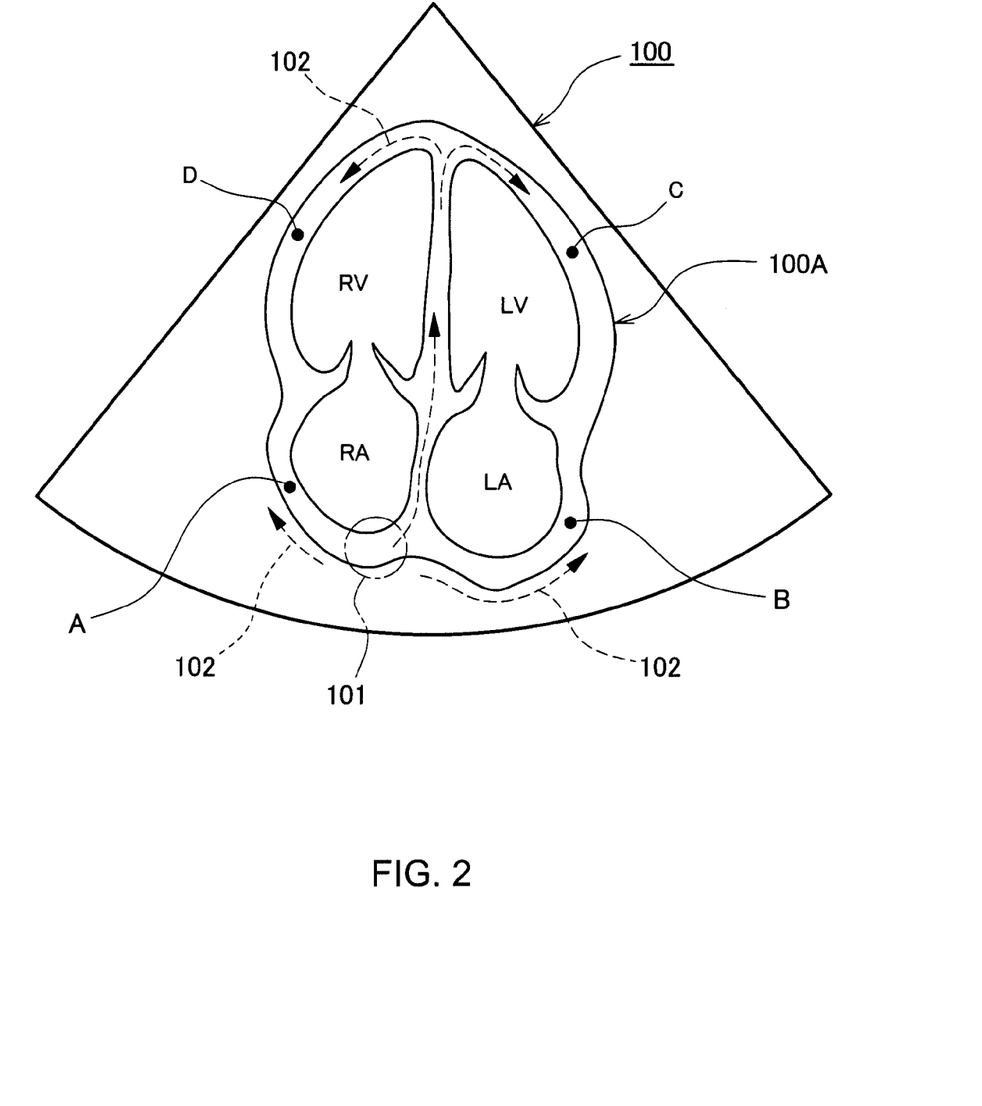
FIG. 2 is a diagram showing a plurality of observation points which are set on a tomographic image of the heart.

FIG. 2 shows a tomographic image 100 representing the heart of the fetus. The tomographic image 100 is a so-called four-chamber cross-sectional image, with the upper part being a cardiac apex. Alternatively, a two-chamber cross-sectional image indicating a long axis view, or other images may be used.

More specifically, in the tomographic image 100, reference numeral 100A represents a cross section of the heart, and, in the cross section, four heart chambers including the right atrium (RA), the right ventricle (RV), the left atrium (LA), and the left ventricle (LV) are shown. Reference numeral 101 represents the sinus node (sinoauricular node), which is a source of the electric signal in the heart and from which the electric signal is sent to the various sites. Reference numeral 102 represents a plurality of signal conduction pathways from the sinus node 101 to the cardiac muscle. The form of the conduction network shown in FIG. 2 is a schematic view, for explaining the invention.

In the present embodiment, when the tomographic image 100 of the heart of the fetus is displayed, the user sets a plurality of observation points. The setting of the observation points is executed on a predetermined initial image (initial frame), and, in the images of the subsequent frames, the position of each observation point (new position) is automatically identified through tracking. In FIG. 2, four observation points A, B, C, and D are set. These positions are merely exemplary for explaining the invention. The observation points are desirably determined as points that are clinically or anatomically significant. In any case, a point proximal in time and a point distal in time from the sinus node 101 are determined, and a time difference of motion in these points is calculated using the method to be described below. Alternatively, two points which are at the same temporal position may be determined.

When the plurality of observation points are determined in a manner described above, in the present embodiment, the pattern matching method is sequentially applied between adjacent frames, and two-dimensional motion vectors between frames are successively calculated for each observation point. That is, the tracking of the motion in the two-dimensional plane is executed for each observation point. As the tracking method, in addition to the pattern matching described above, there may be used a method using the Doppler information, an echo tracking method considering the phase of the RF signal, and other methods. In the present embodiment, a two-dimensional vector is calculated, but alternatively, it is also possible to define a displacement measuring direction for each observation point, and a one-dimensional amount of displacement may be calculated in this direction. In the present embodiment, the pattern matching is executed based on the image information after coordinate conversion, but alternatively, the inter-frame matching process may be applied to the signal before the coordinate conversion or to upstream RF signals.

In any case, in the present embodiment, displacement between frames is successively calculated for each observation point, and a plurality of displacement waveforms corresponding to the plurality of observation points are generated (refer to FIG. 4 to be described later). Each displacement waveform comprises a plurality of displacement data (displacement data array) on the time axis. Prior to the analysis of the displacement waveform, an averaging process or an interpolation process may be applied to the displacement waveform. As will be described below in detail, waveform analysis is individually executed for the displacement waveforms. More specifically, first, a representative point is calculated for each heartbeat in each displacement waveform, and then, a time difference between representative points (time difference of motion) between displacement waveforms is calculated. By determining numerical values or graphing such a time difference of motion, it becomes possible to easily recognize an abnormality in the conducting system of the electric signal or abnormality in the cardiac muscle motion. In particular, because the electrocardiographic signal cannot be directly measured for the heart of the fetus, by executing the multi-point motion analysis based on the image as described above, there is an advantage that the heart function measurement can be executed even for the heart of the fetus. The representative point may be determined as a peak point, an inflection point, a zero-cross point, or other points.

Figure 3:
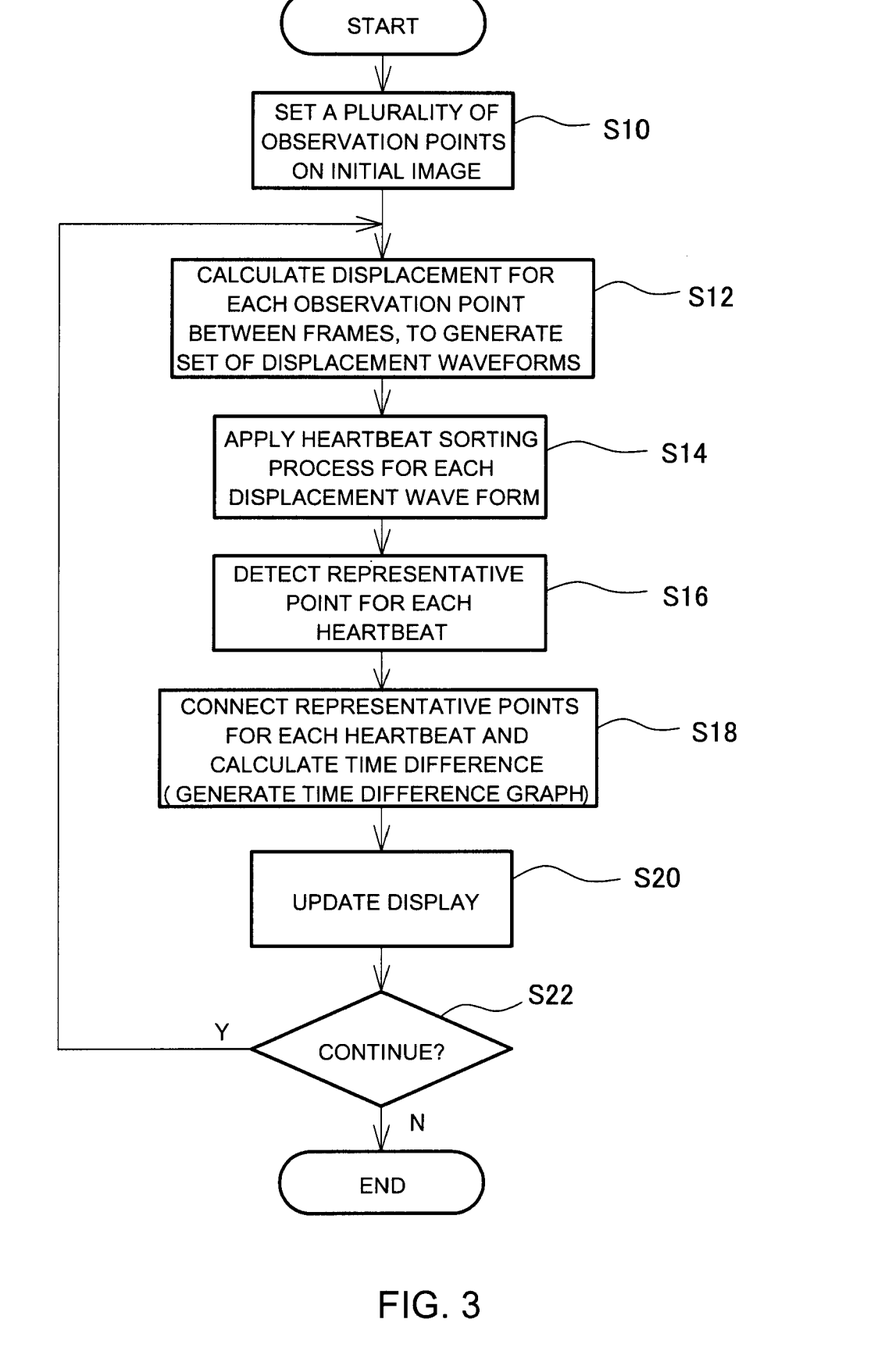
FIG. 3 is a flowchart for explaining a method of calculating a time difference according to a preferred embodiment of the present invention.

FIG. 3 shows a flowchart of specific processes of the conducting system measuring unit shown in FIG. 1. In S10, a tomographic image of the heart of the fetus is displayed. On a sequence of tomographic images, an initial image is designated, and a plurality of observation points are designated by the user on the initial image. The plurality of observation points may be set during a real time measurement, but it is desirable to set the plurality of observation points on a specific image reproduced from the cine-memory. Alternatively, an automated method may be applied including automatic selection of an image of a specific time phase and automatic determination of the observation points. In S12, the motion of the observation points are tracked between frames; that is, the displacement is calculated for each observation point. In this case, the pattern matching method between the frames as described above is applied, and the two-dimensional displacement vector is calculated as the displacement. The displacement vector is calculated for each observation point and for each time phase, and is represented on the time axis as a graph, to generate a plurality of displacement waveforms (displacement waveform array). All of these processes after the designation of the observation points are automatically executed. The horizontal axis in each displacement waveform represents the time axis, which is a common time axis. On the other hand, the vertical axis in each displacement waveform represents an amount of displacement or a degree of displacement, and, in the present embodiment, represents a length of the vector.

In S14, a heartbeat sorting or dividing process is applied for each displacement waveform. More specifically, because the waveform moves up and down in a pulsating manner according to the time phase of the heartbeat, using the characteristic amount, individual heartbeat period is identified, for example, as a period from a valley to a valley or a period from a sign inverting point of the differentiated value to the next sign inverting point of the differentiated value. In this case, various known methods may be employed. In S16, a representative point is detected for each displacement waveform and for each heartbeat. In this case, the representative point may be a peak point, an inflection point, a zero-cross point, or the like. As the representative point, it is desirable to specify a time phase representing a start timing of a local cardiac muscle contraction, and a peak point may be used as such a point.

In S18, on an image in which the plurality of displacement waveforms are arranged in the up and down direction, the representative points adjacent in the up and down direction are connected for each heartbeat, to identify a sequence of representative points which are correlated to each other (arrangement of a plurality of representative points in each heartbeat), and a time difference is calculated between each representative point. In this case, the pair for which the time difference is to be determined may be specified in advance, or may be selected by the user. For example, the time difference is calculated between the point A and the point B, between the point A and the point C, between the point A and the point D, between the point B and the point C, between the point C and the point D, etc. Alternatively, the time difference may be calculated for all combinations. Typically, the time difference is calculated for at least one observation point pair comprising a proximal point and a distal point viewed from the sinus node. In S18, a graph representing the temporal change of such a time difference is generated. On the other hand, a plurality of connecting curves connecting the plurality of representative points in individual heartbeat over or across the plurality of displacement waveforms are generated. Such a connecting curve as an across line is generated for each heartbeat. More specifically, as will be described below, the plurality of horizontal axes of the plurality of displacement waveforms are parallel to each other, and form a common time axis. The plurality of vertical axes of the plurality of displacement waveforms are axes representing the displacement, and are arranged linearly in the up and down direction. In addition, a plurality of connecting curves are displayed across the displacement waveforms in the up and down direction. The plurality of connecting curves are arranged in the time axis direction. In this case, the plurality of displacement waveforms are placed in the order from the upstream side to the downstream side in the conduction pathways of the electric signal, and, thus, the connecting curve is generally represented as a line from the upper right toward the lower left.

In S20, the image and numerical values formed in the above-described manner are displayed, or the displayed content is updated. The steps from S12 are repeatedly executed until it is determined in S22 that the process is to be completed. After the above-described process is completed, the plurality of displacement waveforms and the plurality of connecting curves may be reproduced and displayed using a loop reproduction function. Alternatively, the waveform or the numerical value corresponding to a specific time phase may be individually displayed when the specific time phase is designated.

Figure 4:
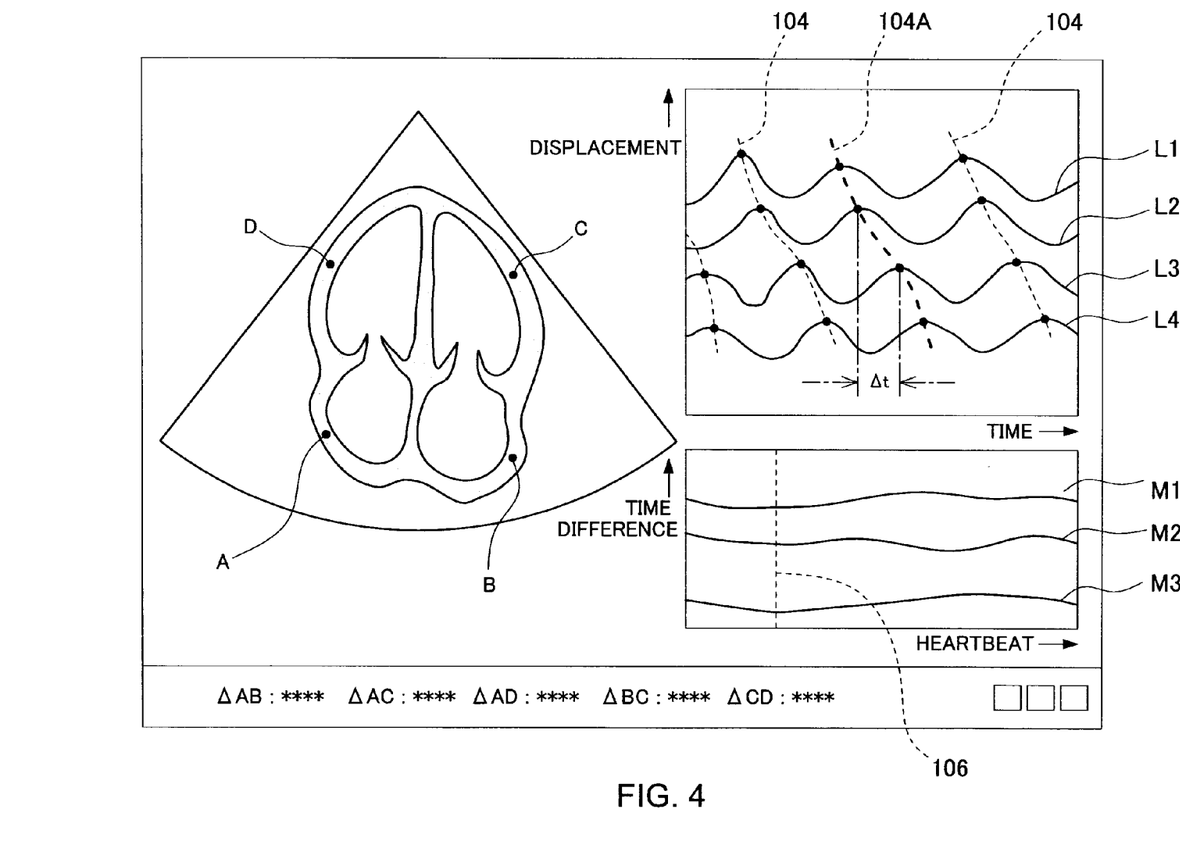
FIG. 4 is a diagram showing an example display.

FIG. 4 shows an example display. On the left side of FIG. 4, a tomographic image is displayed as a first image, and 4 observation points, points A, B, C, and D, are set by the user for the tomographic image. On the top right of FIG. 4, a second image including 4 displacement waveforms is displayed. More specifically, displacement waveforms L1, L2, L3, and L4 are displayed. The horizontal axis represents the time axis, and the vertical axis represents the magnitude of displacement. The plurality of actual vertical axis of the plurality of displacement waveforms are arranged in the up and down direction. Each waveform or each curve shown in FIG. 4 is merely exemplary for explaining the invention.

At the lower right of FIG. 4, a third image including a plurality of graphs M1, M2, and M3 representing the time difference of motion between the observation points is displayed. The horizontal axis represents the heartbeat and the vertical axis represents the time difference. When abnormal signal conduction is suddenly caused, such an abnormality can be easily identified from disturbance in the graph. As shown at the upper right of FIG. 4, a plurality of connecting curves 104 are displayed in an overlapping manner for the plurality of displacement waveforms. Each connecting curve 104 is generated by connecting a plurality of representative points in the up and down directions at each heartbeat. In the present embodiment, one connecting curve 104 is generated through spline interpolation for 4 representative points. On the other hand, a time difference Δt is calculated between two predetermined displacement waveforms, and this process is executed for each observation point pair which is set in advance. By calculating the time difference for such an observation point pair for each heartbeat, it is possible to generate the graphs M1, M2, and M3 described above and generate a fourth image displayed on the lower part of the screen and including a plurality of numerical value displays (time difference displays).

In the example display of FIG. 4, as shown by reference numeral 106, when a specific heartbeat time phase is designated by the user, a numerical value representing the time difference corresponding to the heartbeat time phase is displayed, and, in the second image, the connecting curve corresponding to the designated heartbeat time phase is displayed in a highlighted manner (refer to 104A).

Figure 5:
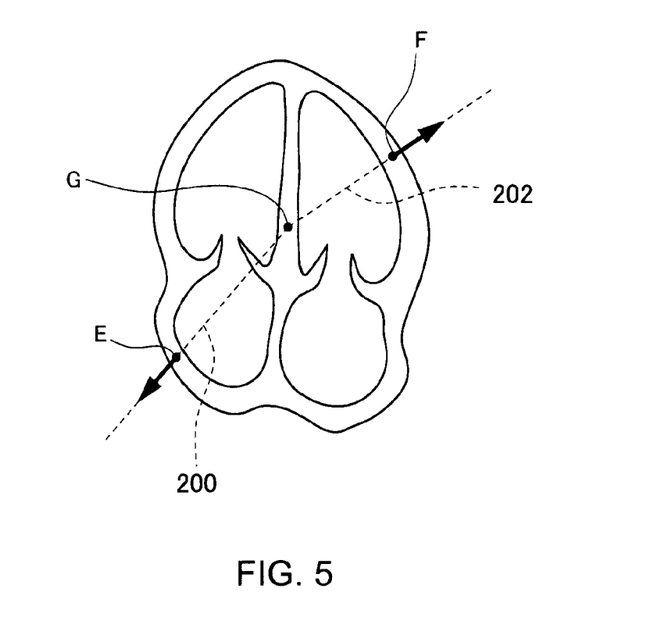
FIG. 5 is a diagram showing an example setting of the displacement measuring direction.

Next, a method of determining a displacement measuring direction will be described with reference to FIGS. 5 and 6. In the above-described embodiment, the two-dimensional displacement vector is calculated between frames for each observation point, and the length of the vector is determined as the displacement. In the example configuration of FIG. 5, a center-of-gravity point G of the heart is measured for each frame, measurement directions 200 and 202 are designated as directions connecting the center-of-gravity point G and observation points E and F, and the displacement components are calculated in the directions 200 and 202 as the inter-frame displacements of the observation points. With such a configuration, even when the heart is moved in a translating motion, because the center-of-gravity G also moves with the translating motion of the heart, the relative motion of each site of the cardiac muscle can be objectively identified without being significantly affected by the translational motion component. In addition, because each a cardiac muscle tissue generally moves in the forward and backward direction with respect to the center of the heart cavity, measurement of the amount of the relative motion with respect to the center of gravity is practical. The calculation of the center-of-gravity point G may be executed as the center of gravity of the overall heart or as the center of gravity of the bloodstream section in the heart. Alternatively, a center of gravity of a specific heart cavity may be calculated.

Figure 6:
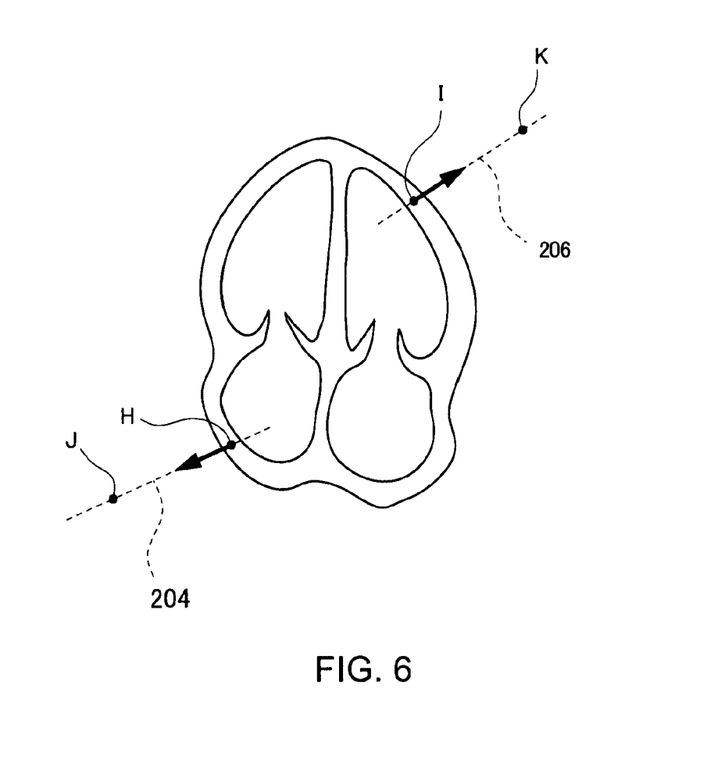
FIG. 6 is a diagram showing another example setting of the displacement measuring direction.

In an example configuration of FIG. 6, points J and K for determining the displacement measuring directions for observation points H and I are designated, and displacement measuring directions 204 and 206 are determined as directions connecting the points J and K. The points J and K may be fixed points on the screen or may be points within or outside the heart. According to this configuration, because the motion component in the specific direction can be observed, an optimal motion component can be observed according to the object of measurement or the like.

The above-described methods are merely exemplary, and in all cases, it is desirable that the displacement be calculated to allow quantitative observation of the motion of the heart wall for each observation point. In the above-described embodiment, 4 observation points are determined, but it is sufficient to determine at least two observation points. For such setting of the plurality of observation points, the plurality of observation points may be determined from the upstream side toward the downstream side along a specific (one line of) signal conducting route in the heart. By determining the observation points in this way, it is possible to obtain an advantage that the heart function can be evaluated, including the conducting abnormality of the signal. However, the observation points can be arbitrarily determined, and the observation points are desirably determined as the most clinically significant points. Alternatively, the observation points may be determined on the sinus node. According to the present embodiment, there can be obtained advantages that behavior of the electric signal in the heart and motion of the local site of the cardiac muscle can be evaluated even for a heart of a fetus for which the electrocardiographic signal cannot be directly obtained, and that the heart of the fetus can be diagnosed before birth.

What is claimed is:
1. An ultrasonic diagnostic apparatus comprising:
a probe configured to transmit and receive ultrasound to and from a heart of a fetus;
a display;
a processor configured to form an ultrasonic image of the heart based on a reception signal obtained by transmission and reception of the ultrasound to and from the heart;
said processor configured to set, on the ultrasonic image of the heart, proximal and distal observation points on conduction pathways of the heart for an electric signal which causes contraction of a cardiac muscle, wherein the proximal observation point is near a source of the electric signal in the heart, and the distal observation point is farther away from the source of the electric signal than the proximal observation point;
said processor configured to track each of the proximal and distal observation points based on the reception signal or the ultrasonic image to determine temporal displacements of each of the proximal and distal observation points;
said processor configured to generate a proximal displacement waveform representing the temporal displacements for the proximal observation point and a distal displacement waveform representing the temporal displacements for the proximal observation point;
said processor configured to display, on said display, a displacement waveform image comprising the proximal displacement waveform and the distal displacement waveform arranged in a predetermined order in parallel to a common time axis;

said processor configured to apply a sorting process to the proximal displacement waveform and the distal displacement waveform by heartbeat period;

said processor configured to detect a representative point representing a proximal contraction timing in each of heartbeats on the proximal displacement waveform which has been sorted by the sorting process and a representative point representing a distal contraction timing in said each of the heartbeats on the distal displacement waveform which has been sorted by the sorting process, wherein the proximal contraction timing is a generation timing of local contraction caused by the electric signal at the proximal observation point, and the distal contraction timing is a generation timing of local contraction caused by the electric signal at the distal observation point;

said processor configured to calculate a time difference of motion for said each of the heartbeats based on the plurality of representative points in said each of the heartbeats;

the processor configured to display, on said display, the time difference of motion of said heartbeats;

said processor configured to connect the plurality of representative points in said each of the heartbeats to generate a plurality of connecting curves; and said processor configured to display, on said display, the plurality of connecting curves across the proximal and distal displacement waveforms.

2. The ultrasonic diagnostic apparatus according to claim 1, wherein said processor is further configured to determine a displacement measuring direction for each of the observation points.

3. The ultrasonic diagnostic apparatus according to claim 2, wherein said processor is further configured to set a reference point inside the heart; and wherein the determination of the displacement measuring direction for each of the observation points comprises determination of the displacement measuring direction relative to the reference point.

4. The ultrasonic diagnostic apparatus according to claim 2, wherein said processor is further configured to set a plurality of reference points outside the heart; and wherein the determination of the displacement measuring direction for each of the observation points comprises determination of the displacement measuring direction relative to a corresponding one of the plurality of reference points.

* * * * *

UNITED STATES PATENT AND TRADEMARK OFFICE
CERTIFICATE OF CORRECTION

PATENT NO.      : 9,119,556 B2
APPLICATION NO. : 13/037538
DATED           : September 1, 2015
INVENTOR(S)     : Masahiko Nakata et al.

It is certified that error appears in the above-identified patent and that said Letters Patent is hereby corrected as shown below:

On the Title page item (73)

Change

(73) Assignee: "HITACHI ALOKA MEDICAL, LTD., Tokyo (JP)"

To be (73) Assignee: -- YAMAGUCHI UNIVERSITY, Yamaguchi-shi (JP)

HITACHI ALOKA MEDICAL, LTD., Tokyo (JP) --

Signed and Sealed this
Fifth Day of April, 2016

Michelle K. Lee
*Director of the United States Patent and Trademark Office*